(12) United States Patent
Tuck

(10) Patent No.: US 8,227,646 B2
(45) Date of Patent: Jul. 24, 2012

(54) PROCESS FOR THE HYDROGENATION OF GLYCEROL TO PROPYLENE GLYCOL

(75) Inventor: Michael William Marshall Tuck, London (GB)

(73) Assignee: Davy Process Technology Limited, Eastbourne Terrace (GB)

( * ) Notice: Subject to any disclaimer, the term of this patent is extended or adjusted under 35 U.S.C. 154(b) by 399 days.

(21) Appl. No.: 12/063,413

(22) PCT Filed: Jul. 17, 2007

(86) PCT No.: PCT/EP2007/057400
§ 371 (c)(1),
(2), (4) Date: Apr. 21, 2010

(87) PCT Pub. No.: WO2008/012244
PCT Pub. Date: Jan. 31, 2008

(65) Prior Publication Data
US 2010/0204527 A1    Aug. 12, 2010

(30) Foreign Application Priority Data
Jul. 26, 2006 (GB) .................................. 0614823.3

(51) Int. Cl.
C07C 27/04 (2006.01)
C07C 29/132 (2006.01)
C07C 29/60 (2006.01)

(52) U.S. Cl. ...................................................... 568/861
(58) Field of Classification Search .................... 568/861
See application file for complete search history.

(56) References Cited

U.S. PATENT DOCUMENTS

| | | | |
|---|---|---|---|
| 5,214,219 A | 5/1993 | Casale et al. | |
| 5,254,758 A * | 10/1993 | Hiles et al. | 568/881 |
| 5,426,249 A | 6/1995 | Haas et al. | |
| 5,616,817 A | 4/1997 | Schuster et al. | |
| 7,355,083 B2 * | 4/2008 | Tuck et al. | 568/861 |

FOREIGN PATENT DOCUMENTS

| | | |
|---|---|---|
| DE | 524101 | 5/1931 |
| DE | 4302464 | 8/1994 |
| WO | WO 2007/010299 | 1/2007 |

OTHER PUBLICATIONS

Chaminand et al., Glycerol hydrogenolysis on heterogeneous catalysts, Green Chem., 2004, pp. 359-361.
Dasari et al., Low-pressure hydrogenolysis of glycerol to propylene glycol, Applied Catalysis A: General 281, 2005, pp. 225-231.

* cited by examiner

Primary Examiner — Brian J Davis
(74) Attorney, Agent, or Firm — Armstrong Teasdale LLP

(57) ABSTRACT

A process for the production of propylene glycol by reaction of a feed material comprises glycerol in the presence of hydrogen which comprising the steps of: (a) supplying a stream comprising the feed material to a first vaporisation zone and contacting said feed with cycle gas comprising hydrogen such that at least a portion of the feed is vaporised by and into the cycle gas; (b) supplying at least a portion of the cycle gas and the vaporised feed material to a first reaction zone comprising catalyst and operating under reaction conditions to allow hydrogenation and dehydration to occur such that a major part of the glycerol is converted; (c) recovering from the first reaction zone an intermediate product stream comprising cycle gas, minor amounts of unconverted glycerol, and desired product(s); (d) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream; (e) supplying the stream from step (d) to a final reaction zone comprising catalyst and operating under reaction conditions to allow hydrogenation and dehydration to occur such that a major part of the glycerol is converted; and (f) recovering from the final reaction zone a final product stream comprising cycle gas, minor amounts of unconverted feed glycerol and the desired product(s).

17 Claims, 1 Drawing Sheet

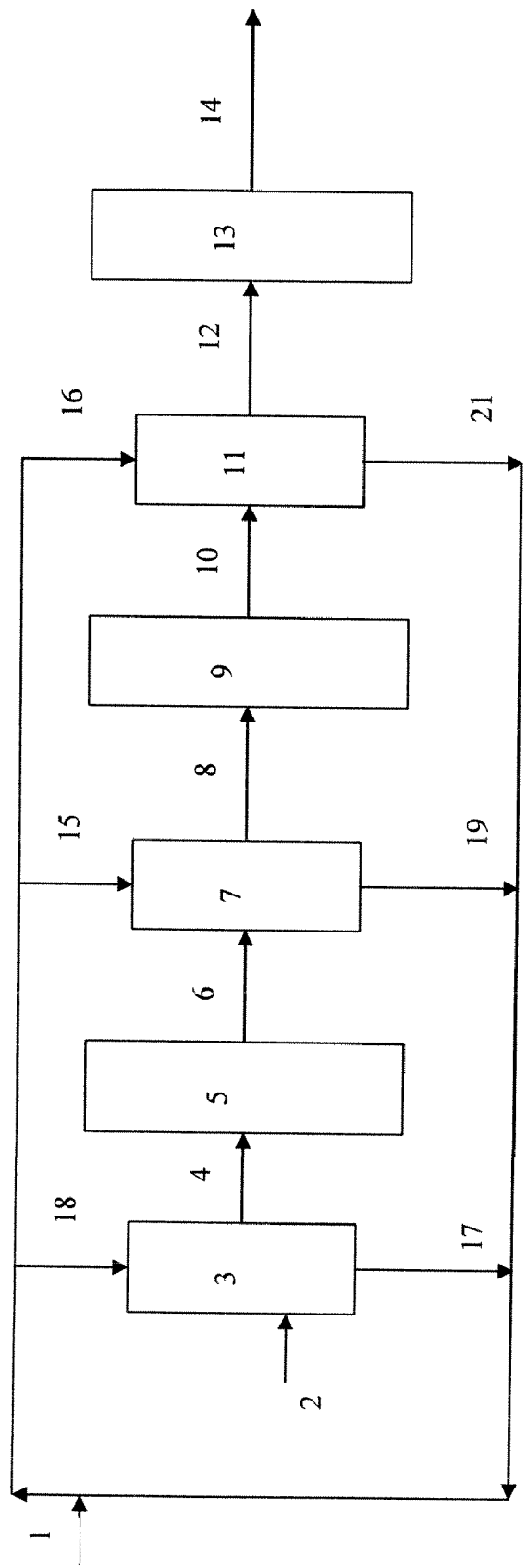

PROCESS FOR THE HYDROGENATION OF GLYCEROL TO PROPYLENE GLYCOL

CROSS REFERENCE TO RELATED APPLICATION

This patent application is a U.S. National Phase patent application of International Application Serial Number PCT/EP2007/057400 filed on Jul. 17, 2007, which claims priority from GB 0614823.3 filed on Jul. 26, 2006.

The present invention relates to a process for hydrogenation in the vapour phase of 1,2,3-propanetriol, also known as glycerol. More particularly it relates to a process which minimises hydrogen circulation requirements while maintaining high selectivity and conversion.

Glycerol is available in large quantities and it is anticipated that the supply of glycerol will increase as it is a by-product of processes which are becoming increasingly attractive since they are based on natural products such as oils and fats as starting materials. Examples of oils and fats include palm oil, rape seed oil, beef tallow and the like.

However, whilst glycerol is available in large quantities its present uses are limited in volume. It is therefore desirable to provide processes which enable the glycerol to be converted to useful materials. It will therefore be understood that coupling downstream processes which use glycerol as a feedstock to processes which have glycerol as a by-product offers economic advantages. Thus processes to which a glycerol reactor could be coupled include bio-diesel units and fat splitters such as feed units to natural detergent plants and the like.

Although glycerol does not have uses to match its availability, it can be converted to 1,2-propanediol and 2-propanol which are valuable materials which have various applications. Thus any new processes that use glycerol as a feedstock serve to improve the economics of processes that have glycerol as a by-product such as bio-diesel units, fat splitters and the like.

Various processes have been proposed for effecting the conversion of glycerol to 1,2-propanediol.

In U.S. Pat. No. 5,426,249, which is incorporated herein by reference, there is described a process in which a gaseous stream of glycerol is dehydrated to acrolein. The acrolein is then condensed and hydrated to 3-hydroxypropionaldehyde which is then subjected to hydrogenation in the liquid phase. This multi-step process enables 1,2- and 1,3-propanediol to be obtained simultaneously.

U.S. Pat. No. 5,214,219, which is incorporated herein by reference, describes a process in which glycerol is converted to 1,2-propanediol and 1,2-ethanediol. In this process hydrogenation of the glycerol is carried out in the liquid phase in the presence of a copper/zinc catalyst and at a temperature of about 220° C.

An alternative processes for the liquid phase hydrogenation of glycerol is described in U.S. Pat. No. 5,616,817, which is incorporated herein by reference. The process, which is directed to the production of 1,2-propanediol, requires the glycerol to have a water content of no more than 20% by weight. The hydrogenation is carried out in the presence of a catalyst comprising cobalt, copper, manganese and molybdenum.

Chaminand et al. Green Chem. 6, (2004) 359-361 describes a process in which the glycerol is hydrogenated in the liquid phase using a supported metal catalyst. At the process conditions of 180° C. and 85 bar the reaction rate is slow with only 20% conversion being achieved after 168 hours.

An alternative process is described in Desari et al Catalysis A281, (2005) 225-231 in which a copper/chrome catalyst is used for the liquid phase hydrogenation of glycerol. However, conversion was low with conversion rates of less than 30% being noted. It is suggested that this is due to the catalyst becoming deactivated and reactivation of the catalyst between tests was required.

DE4302464 and DE524101 describe in detail liquid phase processes for the production of 1,2-propanediol from glycerol. Whilst each makes passing reference to the possibility of the production being carried out in the vapour phase, neither document describes how the process can be efficiently and commercially carried out in the vapour phase to obtain high conversion and selectivity.

A process for the vapour phase hydrogenolysis of glycerol is described in PCT application no PCT/GB2006/050181. This process has benefits in terms of increased conversion and selectivity at low pressure conditions when compared with the equivalent liquid phase processes. Whilst this process offers various benefits over the prior art processes, the low volatility of glycerol requires that large amounts of hydrogen, vastly in excess of the stoichiometric requirements, must be used to maintain the reactor feed in the vapour phase. Whilst the hydrogen consumption can be minimised by separating the stoichiometric excess from the propanediol product and recycling it, there remains an economic penalty associated with compressing, heating and cooling the quantities of hydrogen required.

Whilst the quantities of hydrogen required can be reduced by operating at higher temperatures, the process then suffers from reduced selectivity. There is therefore a need for a process which minimises the hydrogen circulation requirements while maintaining high selectivity and conversion.

SUMMARY OF DISCLOSURE

It has now been discovered that glycerol can be efficiently converted to the desired products with minimisation of the hydrogen requirement by carrying out the reaction in multiple reaction stages.

Thus according to one aspect of the present invention there is provided a process for the production of propylene glycol by reaction of a feed material comprising glycerol in the presence of hydrogen which comprises the steps of:
   (a) supplying a stream comprising the feed material to a first vaporisation zone and contacting said feed with cycle gas comprising hydrogen such that at least a portion of the feed is vaporised by and into the cycle gas;
   (b) supplying at least a portion of the cycle gas and the vaporised feed material to a first reaction zone comprising catalyst and operating under reaction conditions to allow hydrogenation and dehydration to occur such that a major part of the glycerol is converted;
   (c) recovering from the first reaction zone an intermediate product stream comprising cycle gas, minor amounts of unconverted glycerol, and desired product(s);
   (d) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream;
   (e) supplying the stream from step (d) to a final reaction zone comprising catalyst and operating under reaction conditions to allow hydrogenation and dehydration to occur such that a major part of the glycerol is converted; and
   (f) recovering from the final reaction zone a final product stream comprising cycle gas, minor amounts of unconverted feed glycerol and the desired product(s).

By a major part of the glycerol being converted we mean more than 50%, preferably more than 60%, preferably more than 70%, more preferably more than 80%, more preferably more than 85%, still more preferably more than 90%, even more preferably more than 95% and most preferably substantially all of the glycerol is converted.

By means of the process of the present invention, the problems of the prior art processes are obviated and the efficiency and cost-effectiveness of the process is maximised while retaining the desired level of conversion and selectivity.

In a preferred arrangement of the present invention, additional vaporisation and respective reaction zones will be located between the first reaction zone and the final vaporisation zone. Thus the reaction may include further process steps:

(c1) supplying the intermediate product steam from the preceding reaction zone to a subsequent vaporisation zone and contacting it with additional feed material such that an amount of glycerol, approximately equivalent to that vaporised in the preceding vaporisation zone, is vaporised by and into the intermediate product stream;

(c2) supplying the product of step (c1) to a subsequent intermediate reaction zone comprising catalyst and operating under reaction conditions to allow hydrogenation and dehydration to occur so that a major part of the glycerol is converted; and (c3) recovering from the subsequent reaction zone an intermediate product stream comprising cycle gas, minor amounts of unconverted feed glycerol, and the desired products.

"A major part" in step (c2) is as defined above.

Steps (c1) to (c3) may be repeated as often as required. The invention can be carried out with any suitable number of vaporisation zones and associated reaction zones. In a preferred arrangement of the present invention there may be from 2 to 9 vaporisation zones and associated reaction zones, more preferably 3 or 4 vaporisation zones and associated reaction zones.

The optimum number of vaporisation and reaction stages is determined by economic factors which are specific for each plant situation. These factors include the capital cost of the equipment and the operating cost of the reaction process and in particular energy and other utility requirements. Whilst it is acknowledged that increasing the number of stages will add to the capital costs by adding equipment, reducing the cycle gas rate will have the effect of reducing the size and cost of the heat exchangers and interconnecting pipework. In addition, increasing the number of stages will reduce the compressor flow and therefore power consumption. Of course, there is a trade off with the increased number of stages adding to pressure losses in the circuit which will increase the compressor power consumption. Table 1 illustrates the relationship between the number of reaction stages and the cycle gas requirements for a particular ratio of glycerol to hydrogen in the reaction zones. The table also shows how the compressor power requirements go through a minimum as the number of stages is increased.

TABLE 1

| Number of Vaporisation/Reaction Stages | Reaction Zone Hydrogen/Glycerol Ratio | Overall Hydrogen/Glycerol Ratio | Relative Compressor Power Consumption |
|---|---|---|---|
| 1 | 500:1 | 500:1 | 1.00 |
| 2 | 500:1 | 250:1 | 0.71 |
| 3 | 500:1 | 167:1 | 0.57 |
| 4 | 500:1 | 125:1 | 0.51 |
| 5 | 500:1 | 100:1 | 0.47 |
| 6 | 500:1 | 83:1 | 0.46 |
| 7 | 500:1 | 71:1 | 0.46 |
| 8 | 500:1 | 62:1 | 0.46 |
| 9 | 500:1 | 56:1 | 0.47 |

TABLE 1-continued

A surprising feature of the present invention is that it can be operated without incurring a significant loss in selectivity to the desired product, propylene glycol.

The process of the present invention can be carried out at any suitable conditions. The feed material is preferably fed to the first vaporiser where it is partially vaporised in hydrogen containing gas at temperatures of from about 180° C. to about 240° C. One problem associated with utilising glycerol is that it can form extremely viscous residues. In a preferred arrangement of the present invention the amount of hydrogen supplied is controlled such that not all glycerol present is vaporised. Unconverted glycerol is recycled in the system so that there is no overall loss of conversion. Ensuring that some glycerol is not vaporised minimises the formation of residues and allows any residues formed to be purged from the system.

The hydrogen-containing cycle gas supplied to the vaporiser maybe of any suitable composition. In one arrangement, it comprises a major amount of hydrogen and at most a minor amount of one or more inert gases such as nitrogen, methane, and other low molecular weight hydrocarbons such as ethane, propane, n-butane, iso-butane, carbon oxides, neon, argon and the like. The cycle gas may also contain condensable materials such as water and methanol.

The glycerol feed stream may be pure or impure. In particular, the feed may be glycerol produced as a by-product of processes for the hydrolysis, saponification or transesterification of triglycerides. The glycerol feed may also contain materials recycled from a subsequent propylene glycol product refining system. For example, any hydroxypropanone, which is an intermediate in the production of the desired product, retained in the product stream may be separated therefrom and recycled. Water may be added to the glycerol feed.

Any feed material which is not vaporised in the first vaporiser may be recycled to the first or any subsequent vaporiser.

Any suitable ratio of hydrogen to glycerol may be used. Suitable ratios are from about 200:1 to about 1100:1.

Any suitable catalyst may be used in the first reaction zone. In one arrangement of the present invention the catalyst comprises a fixed bed of a reduced promoted copper catalyst such as copper/alumina/manganese, copper chromite, copper silica or copper zinc catalyst, a reduced nickel catalyst or a reduced cobalt catalyst. Whilst a mixture of catalysts may be used, for ease of reference, the term "catalyst" will be used herein and will be understood to mean either a single catalyst or a mixture of two or more different catalysts. The catalyst used in the subsequent reaction zone may be different from that used in the first reaction zone. Where there are more than two reaction zones present, the catalyst used in the, or each, zone may be the same as, or different from, that used in the first and/or subsequent reaction zone.

In one arrangement, a bed comprising a variety of catalysts may be used. Catalyst beds comprising more than one type of catalyst may comprise discrete layers of catalyst within the bed such that different types are separated or the different catalyst types may be admixed.

When the or each catalyst is a copper-containing catalyst, the active catalytic species may be at least partially supported on a supporting material selected from chromia, zinc oxide, alumina, silica, silica-alumina, silicon carbide, zirconia, titania, carbon, or a mixture of two or more thereof, for example, a mixture of chromia and carbon.

Any suitable reaction conditions may be used such that the glycerol is converted to propylene glycol and other products and that the product mixture is substantially free from glycerol. Generally, the conversion of glycerol should be at least about 90%, more preferably it should be at least about 95% and even more preferably about 98% or more.

In one arrangement, the temperature of the, or each, reaction zone may be from about 160° C. to about 260° C., more preferably from about 205° C. to about 220° C. In one arrangement, the temperature of the first reaction zone may be from about 205° C. to about 220° C. and the temperature of the final reaction zone may be from about 180° C. to about 240° C.

The reaction zone may be operated adiabatically and as the reaction of glycerol to propylene glycol is exothermic, the process temperature rises through the reactor. The hot product gas leaving the reaction zone is passed to a subsequent vaporiser where further feed is vaporised. Thus in this arrangement, at least some of the heat required to vaporise the additional glycerol feed material in the subsequent vaporiser is provided from the hot product stream itself.

Any suitable pressure may be used. Pressures of from about 5 to about 40 barg may be suitable.

Any suitable feed rate may be used. Feed rates of liquid hourly space velocities from about 0.1 to about 0.5 $hr^{-1}$ may be used.

BRIEF DESCRIPTION OF THE DRAWING

The present invention will now be described, by way of example, with reference to the accompanying drawings in which:

FIG. 1 is a schematic diagram of a process in accordance with the present invention.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Whilst for convenience, the description and drawing implies separate heat exchange, vaporisation and reaction equipment, it will be understood that some or all of these may be included into a single vessel or each associated vaporisation zone and reaction zone may be contained within a single vessel.

A glycerol containing feed is fed in line 1 and via line 18 to the first vaporiser 3 where it is contacted with the hydrogen containing cycle gas provided in line 2 where it is vaporised by and into the cycle gas stream before being passed in line 4 to a first reactor 5. Any unvaporised glycerol may be removed in line 17 and recycled via lines 18, 15 and 16 to one or more of the vaporisers 3, 7 and 11. Reactor 5 contains a reduced copper catalyst and is operated at a pressure and temperature sufficient to effect reaction and such that substantially all of the glycerol is converted.

The cycle gas stream, which now contains product, is passed in line 6 to a second vaporiser 7. The glycerol feed provided will be added in line 15. The amount of feed vaporised will be approximately equal to that vaporised in the first vaporiser 3. The glycerol and product containing cycle gas is then passed in line 8 to the second reactor 9. Any unreacted glycerol may be removed in line 19 and recycled via lines 18, 15 and 16 to one or more of the vaporisers 3, 7 and 11. Reactor 9 contains a reduced copper catalyst and is operated at a pressure and temperature sufficient to effect reaction and such that substantially all of the glycerol is converted.

The cycle gas stream containing product is passed in line 10 to a third vaporiser 11. The feed provided will be added in line 16. The amount of feed vaporised will be approximately equal to that vaporised in the second vaporiser 7. Any unvaporised glycerol may be removed in line 21 and recycled via lines 18, 15 or 16 to one of the vaporisers 8, 7 and 11. The glycerol and product containing cycle gas is then passed in line 12 to the third reactor 13. Reactor 13 contains a reduced copper catalyst and is operated at a pressure and temperature sufficient to effect reaction and such that substantially all of the glycerol is converted.

The cycle gas containing product and by-product is then removed in line 14 and treated as appropriate.

The present invention will now be further described with reference to the following examples.

EXAMPLES 3-7

The examples are continuous processes performed on copper based catalysts packed into a 0.75" tubular reactor. The catalyst was then reduced according to conventional means.

The feed material was fed into a heated vessel with the required amount of hydrogen gas at the reaction pressure. This caused complete vaporisation of the feed mixture prior to the resulting stream being passed over the catalyst. The reaction conditions are set out in Table 2, the feed analysis in Table 3 and the product analysis in Table 4.

COMPARATIVE EXAMPLES 1-2

The process of Example 3 was repeated with propylene glycerol as feed. It would generally be expected, partially in the light of the teaching in the prior art, that the use of multiple vaporisers would lead to a loss of selectivity. It is noted from these comparative examples that when propylene glycerol is run through there is a loss. However by comparison with the data for Examples 3 to 7 the surprising benefit that adding glycerol feed to each vaporiser overcomes the problem and the loss is not noted.

TABLE 2

| Example 1 | Comparative Example 1 | Comparative Example 2 | 3 | 4 | 5 | 6 | 7 |
|---|---|---|---|---|---|---|---|
| Feed | Propylene Glycol | Propylene Glycol + 10% water | Glycerol | Glycerol | Glycerol + 10% water | Second zone glycerol feed | Third zone glycerol feed |
| Total Bed Volume, 1 | 0.283 | 0.283 | 0.283 | 0.1 | 0.1 | 0.1 | 0.1 |
| Bed Wt, kg | 0.410 | 0.410 | 0.410 | 0.089 | 0.089 | 0.089 | 0.089 |
| Temp Inlet to Bed ° C. | 199 | 199 | 199 | 210 | 210 | 211 | 210 |
| Temp Bed Exit ° C. | 201 | 200 | 206 | 215 | 215 | 217 | 216 |

TABLE 2-continued

| Example 1 | Comparative Example 1 | Comparative Example 2 | 3 | 4 | 5 | 6 | 7 |
|---|---|---|---|---|---|---|---|
| Pressure, bar | 19.7 | 19.7 | 19.7 | 20.0 | 20.0 | 19.7 | 19.7 |
| Recycle rate g/hr$^{-1}$ | 1204 | 1206 | 1203 | 400 | 399 | 400 | 401 |
| Recycle rate NLPH | 12446 | 12762 | 12565 | 4407 | 4397 | 4402 | 4401 |
| Residence Time, s$^{-1}$ | 0.98 | 0.96 | 0.96 | 0.95 | 0.95 | 0.94 | 0.95 |
| Hydrogen to glycerol ratio | 458 | 422 | 489 | 520 | 521 | 467 | 487 |
| Total hours on line | 1294 | 1325 | 1048 | 16666 | 1709 | 2053 | 2195 |
| LHSV | 0.379 | 0.422 | 0.296 | 0.276 | 0.281 | 0.307 | 0.295 |
| Feed wt g/h | 111.4 | 124.2 | 105.5 | 34.8 | 38.5 | 76.8 | 109.3 |
| Product we per hour, g | 116.0 | 128.8 | 105.4 | 34.6 | 38.9 | 83.5 | 116.5 |

TABLE 3

| | 1 | 2 | 3 | 4 | 5 | 6 | 7 |
|---|---|---|---|---|---|---|---|
| Feed Density | 1.04 | 1.04 | 1.26 | 1.26 | 1.23 | 1.26 | 1.26 |
| Methanol | | | | | | 0.29 | 0.40 |
| Water | | 10.00 | | | 10.00 | 12.44 | 14.01 |
| Ethanol | | | | | | 0.12 | 0.17 |
| 2-propanol | | | | | | 0.47 | 0.58 |
| 1-propanol | | | | | | 0.34 | 0.45 |
| Hydroxypropanone | | | | | | 0.71 | 1.09 |
| Ethylene glycol | | | | | | 0.45 | 0.63 |
| Propylene glycol | 100.00 | 90.00 | | | | 34.78 | 48.65 |
| Glycerol | | | 100.00 | 100.00 | 90.00 | 50.41 | 33.99 |
| 1-heptanol | | | | | | | 0.01 |
| Others | | | | | | 0.00 | 0.04 |
| Total | 100.00 | 100.00 | 100.00 | 100.00 | 100.00 | 100.00 | 100.00 |

TABLE 4

| | 1 | 2 | 3 | 4 | 5 | 6 | 7 |
|---|---|---|---|---|---|---|---|
| Methanol | 0.25 | 0.18 | 1.01 | 0.67 | 0.58 | 0.61 | 0.59 |
| Water | 2.68 | 9.43 | 18.06 | 17.93 | 24.14 | 20.77 | 19.92 |
| Ethanol | 0.94 | 0.61 | 0.79 | 0.31 | 0.23 | 0.23 | 0.25 |
| Acetone | | | | 0.04 | 0.03 | | |
| 2-propanol | 1.67 | 1.20 | 1.73 | 1.25 | 0.90 | 0.83 | 0.82 |
| 1-propanol | 0.97 | 0.88 | 1.29 | 0.80 | 0.65 | 0.65 | 0.67 |
| 2-butanol | | | | | | | |
| Hydroxypropanone | 0.82 | 0.93 | 1.11 | 1.59 | 1.43 | 1.62 | 1.68 |
| 1-butanol | | | | | | | |
| Ethylene glycol | 0.04 | | 1.44 | 0.99 | 0.89 | 0.92 | 1.03 |
| Propylene glycol | 90.39 | 85.54 | 72.63 | 75.77 | 70.32 | 73.02 | 74.25 |
| 1-pentanol | 0.10 | 0.05 | 0.06 | | | | |
| 3-hexanol | | | | | | | |
| 2-hexanol | 0.12 | 0.06 | 0.07 | | | | |
| 1,2-butanediol | 0.69 | 0.38 | 0.47 | | | | |
| 1-hexanol | | | 0.05 | | | | |
| Glycerol | | | 0.32 | 0.61 | 0.83 | 1.35 | 0.78 |
| 1-heptanol | | | | 0.03 | | | |
| 2,5-hexanediol | | | | | | | |
| Others | 1.33 | 0.74 | 0.97 | 0.02 | 0.01 | | |

The invention claimed is:

1. A process for the production of propylene glycol by reaction of a feed material comprising glycerol in the presence of hydrogen which comprises the steps of:
   (a) supplying a stream comprising the feed material to a first vaporisation zone and contacting said feed with cycle gas comprising hydrogen such that at least a portion of the feed is vaporised by and into the cycle gas;
   (b) supplying at least a portion of the cycle gas and the vaporised feed material to a first reaction zone comprising catalyst and operating under reaction conditions to allow hydrogenation and dehydration to occur such that a major part of the glycerol is converted;
   (c) recovering from the first reaction zone an intermediate product stream comprising cycle gas, minor amounts of unconverted glycerol, and propylene glycol;
   (d) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream;
   (e) supplying the stream from step (d) to a final reaction zone comprising catalyst and operating under reaction conditions to allow hydrogenation and dehydration to occur such that a major part of the glycerol is converted; and
   (f) recovering from the final reaction zone a final product stream comprising cycle gas, minor amounts of unconverted feed glycerol and propylene glycol.

2. A process according to claim 1 wherein the reaction conditions in step (b) and/or step (e) allow substantially all of the glycerol to be converted.

3. A process according to claim 1 additionally including the following steps between steps (c) and (d):
   (c1) supplying the intermediate product steam from the preceding reaction zone to a subsequent vaporisation zone and contacting it with additional feed material such that an amount of glycerol, approximately equivalent to that vaporised in the preceding vaporisation zone, is vaporised by and into the intermediate product stream;
   (c2) supplying the product of step (c1) to a subsequent intermediate reaction zone comprising catalyst and operating under reaction conditions to allow hydrogenation and dehydration to occur so that a major part the glycerol is converted; and
   (c3) recovering from the subsequent reaction zone an intermediate product stream comprising cycle gas, minor amounts of unconverted feed glycerol, and propylene glycol.

4. A process according to claim 3 wherein the reaction conditions in step (c2) allow substantially all of the glycerol to be converted.

5. A process according to claim 3 wherein steps (c1) to (c3) are repeated.

6. A process according to claim 5 wherein there are from 3 to 9 vaporisation zones and associated reaction zones.

7. A process according to claim 6 wherein there are 3 or 4 vaporisation zones and associated reaction zones.

8. A process according to claim 1 wherein the feed material is fed to the first vaporiser where it is partially vaporised in hydrogen containing gas at temperatures of from about 180° C. to about 240° C.

9. A process according to claim 1 wherein any feed material which is not vaporised in the first vaporiser is recycled to the first or any subsequent vaporiser.

10. A process according to claim 1 wherein the ratio of hydrogen to glycerol is from about 200:1 to about 1100:1.

11. A process according to claim 1 wherein the catalyst is a reduced copper catalyst, a reduced nickel catalyst or a reduced cobalt catalyst.

12. A process according to claim 1 wherein the temperature of at least one of the first reaction zone in step (b) and the final reaction zone in step (e) is from about 160° C. to about 260° C.

13. A process according to claim 1 wherein the temperature of at least one of the first reaction zone in step (b) and the final reaction zone in step (e) is from about 205° C. to about 220° C.

14. A process according claim 1 wherein the temperature of at least one of the first reaction zone in step (b) and the final reaction zone in step (e) is from about 180° C. to about 240° C.

15. A process according to claim 1 wherein at least one of the first reaction zone in step (b) and the final reaction zone in step (e) is operated adiabatically.

16. A process according to claim 1 wherein the pressure is from about 5 to about 40 barg.

17. A process according to claim 1 wherein the feed rate is a liquid hourly space velocity of from about 0.1 to about 0.5 $hr^{-1}$.

* * * * *